United States Patent [19]

Crounse

[11] 3,935,195

[45] Jan. 27, 1976

[54] 4,4'-STILBENEBIS-PYRIDOOXAZOLES AND RELATED OPTICAL BRIGHTENERS AND POLYMERIC COMPOSITIONS BRIGHTENED THEREBY

[75] Inventor: Nathan N. Crounse, Cincinnati, Ohio

[73] Assignee: Sterling Drug Inc., New York, N.Y.

[22] Filed: July 14, 1971

[21] Appl. No.: 162,620

Related U.S. Application Data

[62] Division of Ser. No. 820,005, April 28, 1969.

[52] U.S. Cl. ................... 260/240 CA; 117/33.5 R; 252/301.2 W; 260/296 H
[51] Int. Cl.$^2$ ........................................ C07D 221/00
[58] Field of Search .. 260/240 CA, 301.2 W, 296 H

[56] References Cited
UNITED STATES PATENTS

| 3,322,680 | 5/1967 | Hedberg et al. | 260/301.2 W |
|---|---|---|---|
| 3,586,673 | 6/1971 | Bloom et al. | 260/240 CA |
| 3,712,888 | 1/1973 | Kaempfen | 260/240 CA |

FOREIGN PATENTS OR APPLICATIONS

| 1,120,454 | 12/1961 | Germany | 260/296 H |
|---|---|---|---|
| 856,319 | 12/1960 | United Kingdom | 260/240 CA |
| 1,026,368 | 4/1966 | United Kingdom | 260/240 CA |
| 1,062,257 | 3/1967 | United Kingdom | 260/240 CA |
| 1,081,876 | 9/1963 | United Kingdom | 260/240 CA |

OTHER PUBLICATIONS

Rochling et al, Chem. Ber. Vol. 104, pp. 344–347 (1971).

Chemical Abstracts, Vol. 73, Abst. No. 110912 (1970).

Chemical Abstracts, Vol. 75, Abst. No. 99260t (1971).

*Primary Examiner*—John D. Randolph
*Attorney, Agent, or Firm*—Lynn T. Fletcher; B. Woodrow Wyatt

[57] ABSTRACT

4,4'-Stilbenebis-2-oxazolopyridines, -2-thiazolopyridines, and 2-imidazopyridines are optical brightening agents useful for whitening and brightening natural and synthetic fibers, papers, resins and the like. The compounds are conveniently prepared by interacting 4,4'-stilbenedicarboxylic acid or its acid chloride with a vicinal disubstituted pyridine compound consisting of vic-aminohydroxypyridine, vic-aminomercaptopyridine or vic-diaminopyridine, respectively.

7 Claims, No Drawings

4,4'-STILBENEBIS-PYRIDOOXAZOLES AND RELATED OPTICAL BRIGHTENERS AND POLYMERIC COMPOSITIONS BRIGHTENED THEREBY

This application is a division of my prior copending application Ser. No. 820,005, filed Apr. 28, 1969.

This invention relates to novel compositions of matter classified in the art of chemistry as heterocyclic-substituted stilbenes and to methods for preparing them. More particularly the invention relates to novel oxazolopyridinyl, thiazolopyridinyl and imidazolopyridinyl derivatives of stilbene useful as optical whitening and brightening agents for natural and synthetic fibers, papers, resins, and the like.

In its composition aspect the present invention resides in the concept of novel chemical compounds having the general structural formula

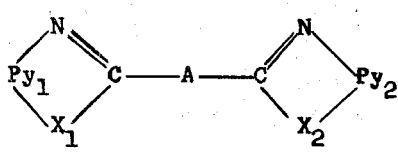

Formula I wherein $Py_1$ and $Py_2$ are each a bivalent heterocyclic nucleus of the pyridine class in which the open bonds are on vicinal ring carbon atoms of said nucleus and $X_1$ and $X_2$ are each a member of the class consisting of O, S and NR, wherein R is a member of the group consisting of H, lower alkyl, hydroxy-lower alkyl, hydromyonaalkyl, phenyl-lower alkyl, cyano-lower alkyl, carboxy-lower alkyl, carbo-lower alkoxy-lower alkyl, phenylhydroxy-lower alkyl and lower alkenyl, and A is a bivalent 4,4'-stilbene radical. In accordance with this aspect of the invention, attached at the 4 and 4'-positions of a stilbene radical, my new compounds have the same or different heterocyclic radical selected from the following class: 2-oxazolo[5,4-b]pyridyl, 2-oxazolo[5,4-c]pyridyl, 2-oxazolo]4,5-b]pyridyl, 2-oxazolo[4,5-c]pyridyl, 2-thiazolo-[5,4-b]pyridyl, 2-thiazolo[5,4-c]pyridyl, 2-thiazolo[4,5-b]-pyridyl, 2-thiazolo[4,5-c]pyridyl, 2-imidazo[4,5-b]pyridyl, and 2-imidazo[4,5-c]pyridyl. Compounds of this class have been found to have unexpectedly superior fluorescent properties when used as whitening and brightening agents and, in addition, have high stability to heat, light, chlorine-type bleaches, and resin-finish catalysts, which make them particularly useful for whitening and brightening textile materials.

In Formula I above $Py_1$ and $Py_2$ are each a heterocyclic nucleus of the pyridine class. Thus, $Py_1$ and $Py_2$ can be the same or different and are selected from the class consisting of pyridine and pyridine substituted by one or more monovalent substituents which tend to increase the solubility of the resulting compound in synthetic resins and fibers. Such substituents include H, lower alkyl and halogen; that is, chlorine, bromine, iodine and fluorine. The aforementioned substituents have the advantage of increasing solubility in synthetic resins without, however, tending to impart color to the resulting compound; that is, they are not auxochromic substituents. The compounds of my invention are strongly fluorescent and are used as optical whitening and brightening agents in high dilution. Therefore they may have slight color without impairing the overall whitening effect. However, auxochromic substituents tend to impart too much color to the compound and thus lessen its value as a whitening agent.

In Formula I above $X_1$ and $X_2$ are members of the class consisting of O, S, and NR. When $X_1$ or $X_2$ is NR, R is H; lower alkyl, preferably containing from 1 to 6 carbon atoms; hydroxy-lower alkyl, preferably containing from 2 to 6 carbon atoms; hydroxyoxaalkyl, preferably containing from 3 to 15 carbon atoms; phenyl-lower alkyl, preferably containing from 7 to 11 carbon atoms; cyano-lower alkyl, preferably containing from 3 to 6 carbon atoms; carboxy-lower alkyl, preferably containing from 2 to 6 carbon atoms; carbo-lower alkoxy-lower alkyl, preferably containing a total of from 3 to 12 carbon atoms; phenylhydroxy-lower alkyl, preferably containing from 8 to 11 carbon atoms; or lower alkenyl, preferably containing from 3 to 6 carbon atoms.

When R is lower alkyl there are included, for example, methyl, ethyl, n-propyl, isopropyl, n-butyl, isoamyl, n-hexyl, and the like. When R is hydroxy-lower alkyl, there are included, for example 2-hydroxyethyl, 2-hydroxypropyl, 2,3-dihydroxypropyl, and the like. When R is hydroxyoxaalkyl there are included, for example, 2-hydroxy-3-(2,3-dihydroxypropoxy)propyl, 2-hydroxy-3-(2 -hydroxyethoxy)propyl, 2-hydroxy-3-[2-(2-hydroxyethoxy)ethoxy]propyl, and the like. When R is phenyl-lower alkyl there are included, for example, benzyl, phenethyl, 3-phenylpropyl, 3-phenylpentyl, and the like. When R is cyano-lower alkyl there are included, for example, 2-cyanoethyl, 3-cyanopropyl, 4-cyanopentyl, and the like. When R is carboxy-lower alkyl there are included, for example, carboxymethyl, 2-carboxyethyl, 3-carboxypropyl, 5-carboxypentyl, and the like. When R is carbo-lower alkoxy-lower alkyl there are included, for example, carbomethoxymethyl, 2-carbomethoxyethyl, 2-carbobutoxyethyl, 3-carbohexyloxypropyl, 5-carbomethoxypentyl, and the like. When R is phenylhydroxy-lower alkyl there are included, for example, β-phenyl-β-hydroxyethyl, α-phenyl-β-hydroxyethyl, β-phenyl-β-hydroxypropyl, and the like. When R is lower alkenyl there are included, for example, allyl, methallyl, 3,3-dimethylallyl, and the like.

In Formula I above, A is a bivalent 4,4'-stilbene radical of the formula

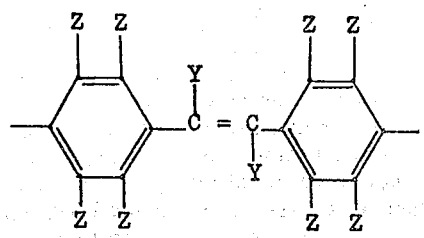

wherein the substituents represented by the term Z are the same or different monovalent substituents bound to the benzene ring by a covalent bond. Z can be any such substituent which does not destroy the desirable fluorescent properties of the compound as a whole. Typical examples of such substituents represented by Z are H; halogen, i.e., chlorine, bromine, iodine and fluorine; lower alkyl, as defined above, for example, methyl, ethyl, propyl, n-butyl, tert.-butyl, amyl, sec.amyl and hexyl; lower alkoxy, for example, methoxy, ethoxy, propoxy, isopropoxy, hexyloxy and the like; aryloxy, wherein the aryl moiety is a one- or two-ring carbocyclic aromatic radical, for example, phenoxy, naphthyloxy, p-chlorophenoxy, and the like; lower alkanesulfonyl wherein the lower alkane moiety contains from one to about six carbon atoms, for example, methanesulfonyl, ethanesulfonyl, butanesulfonyl, and hexanesulfonyl; arenesulfonyl wherein the arene moiety is a one- or two-ring carbocyclic aromatic radical, for example, benzenesulfonyl, p-toluenesulfonyl, $\beta$-naphthalenesulfonyl, and the like; sulfamyl; N-substituted sulfamyl, for example, N,N-dimethylsulfamyl, N-ethylsulfamyl, N-phenylsulfamyl and the like; cyano; carbamyl, and N-substituted carbamyl, for example, N,N-dimethylcarbamyl, N,N-dibutylcarbamyl, N-phenyl-N-methylcarbamyl, N-(2-naphthylcarbamyl) and the like.

The substituents represented by the term Y are the same or different monovalent substituents selected from the group consisting of H; alkyl of from 1 to 18 carbon atoms, for example methyl, ethyl, n-butyl, isobutyl, 2-ethylhexyl, n-pentyl, n-decyl, n-dodecyl, and cetyl; and cyano.

Normally no more than one or two of the substituents Y and Z above are other than H, because the simpler 4,4'-stilbene-disubstituted compounds are cheaper and more easily prepared and are as good or better fluorescent brightening agents than the more highly substituted compounds.

In another of its aspects, the present invention resides in the concept of a process for preparing the compounds depicted in Formula I which comprises interacting a 4,4'-stilbenedicarboxylic acid compound with a vicinal-disubstituted pyridine compound consisting of a vic-aminohydroxypyridine (vic-aminopyridinol), a vic-aminomercaptopyridine (vic-aminopyridinethiol) or a vic-diaminopyridine compound. The reaction takes place by heating said reactants under conditions conducive to the elimination of four molecular equivalents of water. Two reactions are involved in this process, the first being the formation of a 4,4'-stilbenebiscarboxamide intermediate, and the second being a cyclization of the intermediate to the final heterocyclic compound. The process can be carried out in such a manner that the intermediate carboxamide is isolated, or, if desired, the cyclization reaction can be carried out directly without isolation of the intermediate.

In still another of its aspects, the present invention resides in the concept of a process for preparing the compounds depicted in Formula I which comprises interacting a 4,4'-stilbenedicarbonyl chloride compound with a vicinal-disubstituted pyridine compound consisting of a vic-aminohydroxypyridine, a vic-aminomercaptopyridine or a vic-diaminopyridine compound. The reaction takes place by heating the reactants under conditions conducive to the elimination of first of two molecular equivalents of hydrogen chloride and then of two molecular equivalents of water. The first reaction involves the formation of the above-mentioned 4,4'-stilbenebiscarboxamide which is subsequently cyclized to the desired heterocyclic product. This reaction can be carried out with isolation of the 4,4'-stilbenebiscarboxamide or, if desired, the cyclization can be carried out directly without isolation of the intermediate.

In general, the compounds of the above structure are high melting yellow to yellow-green solids which have the following solubility characteristics. They are insoluble in water, hydrocarbons, halogenated aliphatic hydrocarbons, ketones, ethers and the lower aliphatic alcohols. They are generally slightly soluble in hot dimethylformamide, benzyl alcohol and the higher boiling halogenated hydrocarbons such as trichlorobenzene and chlorinated biphenyl. They are moderately soluble in some mineral acids, for example cold sulfuric acid and hot polyphosphoric acid, but they are usually precipitated in their acid addition salt form when the acid solution is diluted with water. The compounds wherein $X_1$ or $X_2$, or both, are NH are generally soluble in alcoholic alkali metal hydroxides, amides, and alkoxides, presumably due to teh formation of the soluble alkali metal salt form.

A preferred class of compounds of this invention comprise compounds of the structure of Formula II

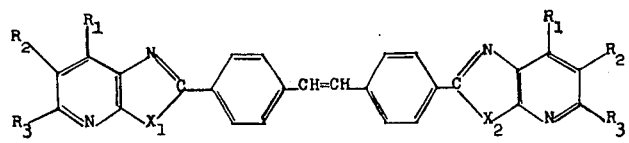

Formula II wherein each of $R_1$, $R_2$, and $R_3$ is a member of the class consisting of H, halogen, lower alkoxy and lower alkyl, and $X_1$ and $X_2$ are as defined above in Formula I.

A particularly preferred class of compounds of the invention are the oxazolopyridines of Formula I wherein $X_1$ and $X_2$ are each 0. These compounds are preferred because of their superior fluorescence and stability and the relative easy of production of members of this class. A particularly preferred compound within this class is 4,4'-stilbenebis(2-oxazolo[5,4-b]pyridine) of the formula

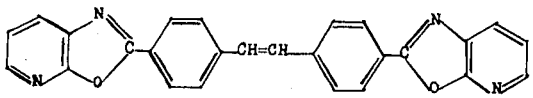

Formula III which possesses an unusually high degree of fluorescence under ultraviolet light at a wavelength of maximum emission of 440 nm when dispersed in polyethylene terephthalate. Moreover this compound is unusually stable to the effects of heat and light, and is thus well adapted for incorporation into textile fiber spinning melts.

Characteristic of compounds containing a pyridine ring, the compounds of this invention react with mild oxidizing agents and with alkylating agents with the formation, respectively, of N-oxides and quaternary ammonium salts. These compounds tend to be somewhat more soluble in polar solvents than their respective parent compounds. Although the fluorescence of these compounds is somewhat weaker than that of the parent amines, the N-oxides and quaternary ammonium salts are useful brightening agents which are effective for the purposes described above.

The manner and process of making and using my invention will now be described so as to enable any person skilled in the art to which it pertains to make and use the same, as follows:

The novel fluorescent compounds of my invention can be prepared by any of several methods. One such process comprises heating 4,4'-stilbenedicarboxylic acid chloride (4,4'-stilbenedicarbonyl chloride) with an aminopyridine compound which has in a position vicinal to the amino group an hydroxyl, mercapto or amino group, whereupon there is formed, respectively, N,N'-bis(orthohydroxypyridyl)-4,4'-stilbenedicarboxamide, N,N'-bis(orthomercaptopyridyl)-4,4'-stilbenedicarboxamide or N,N'-bis(orthoaminopyridyl)-4,4'-stilbenedicarboxamide. The reaction is carried out by heating the reactants in a suitable inert solvent, for example, toluene, chlorobenzene, dioxane, benzene, xylene and the like. As will be obvious to one skilled in the art, this type of reaction proceeds under a wide variety of conditions. We prefer to reflux the reactants in a solvent such as that described above with or without the addition of an acid acceptor. Of course, the reactant itself can serve as an acid acceptor inasmuch as the pyridine compound is basic. The reaction is usually complete in four to eight hours. The resulting pyridylstilbenedicarboxamide compound is cyclized with or without isolation by heating it to a temperature of 175°–250° C. in a high boiling solvent, for example, trichlorobenzene, mineral oil, quinoline, or a eutectic mixture of diphenyl ether and biphenyl, in the presence of a strong acid, for example, p-toluene sulfonic acid. Alternatively, the pyridylstilbenedicarboxamide compound can be cyclized by heating the compound in polyphosphoric acid at about 200° C. It is convenient to follow the progress of the cyclization reaction by means of the ultraviolet absorption spectra of small samples of the reaction mixture taken during the course of the reaction. Because the cyclization results in the formation of a new heteroaromatic ring, the ultraviolet absorption changes perceptibly as the reaction proceeds. The reaction is deemed complete when the spectra of two consecutive samples are the same.

In accordance with this invention, the compounds of Formula I can also be prepared in one step by heating stilbenedicarboxylic acid with a vicinal substituted aminopyridine compound mentioned above in polyphosphoric acid, whereupon condensation and cyclization occur simultaneously. The reaction is carried out by rapidly stirring the reactants while they are heated to a temperature of 125° to 225° C. for approximately 4 to 8 hours. The product is isolated by pouring the reaction mixture into a large excess of ice and water, neutralizing the excess acid, and collecting the precipitate in conventional fashion.

In accordance with another process for preparing the compounds of my invention, o-aminohydroxypyridine, o-aminomercaptopyridine, or o-diaminopyridine is heated with p-toluic acid in polyphosphoric acid at approximately 225°–275° C. for 48 hours to provide, respectively, a 2-p-tolyloxazolopyridine, 2-p-tolythiazolopyridine or 2-p-tolylimidazopyridine. These latter compounds are conveniently converted into corresponding stilbene compounds by the conventional "sulfur melt" method described in the prior art, which comprises heating the tolylsubstituted reactant in molten sulfur at about 250° C. for approximately 6–8 hours.

The preferred compound of Formula III can be prepared in accordance with still another process, as follows. By condensing 3-amino-2-chloropyridine instead of 3-amino-2-pyridinol with 4,4'-stilbenedicarbonyl chloride under the conditions described above, there is obtained the intermediate N,N'-bis(2-chloro-3-pyridyl)-4,4'-stilbenedicarboxamide. This compound is conveniently cyclized to 4,4'-stilbenebis(2-oxazolo[5,4b]pyridine) by heating it at approximately 150°–200° C. with two molecular equivalents of a copper (II) salt and an amine in an inert solvent. Depending upon the temperature the reaction is usually complete in approximately four to eight hours. The nature of the copper (II) salt is not critical; for example, cupric chloride, cupric sulfate, or cupric acetate may be used, but I have found cupric acetate to be convenient for economical reasons. Pyridine is the most convenient amine, but ammonia or alkyl-substituted amine can also be used. Suitable inert solvents include nitrobenzene, o-dichlorobenzene, trichlorobenzene, naphthalene, and dimethylformamide.

The 4,4'-stilbenebis(2-imidazo[4,5-b]pyridine) and 4,4'-stilbenebis(2-imidazo[4,5-c]pyridine) prepared in accordance with the general procedures described above react readily with alkylating agents to yield N-mono and N,N'-di (alkyl or substituted alkyl) derivatives which are useful whitening or brightening agents of Formula I wherein $X_1$ and $X_2$ are N-R and R is alkyl or substituted alkyl radical of the type hereinabove described. The alkylation reaction is readily carried out by heating 4,4'-stilbenebis(2-imidazo[4.5-b]pyridine) or 4,4'-stilbenebis(2-imidazo[4,5-c]pyridine)(Formula I wherein $X_1$ and $X_2$ are each NH) with the appropriate alkylating agent. Usually a heating period of about two to six hours at 50°–150° C. is sufficient to produce a satisfactory yield of the desired product. Alkylating agents useful for this reaction include, for example, esters of strong organic and inorganic acids having the formula R-An wherein R is a member of the class consisting of lower alkyl, hydroxy-lower alkyl, hydroxyoxaalkyl, phenyl-lower alkyl, cyano-lower alkyl, carboxy-lower alkyl, carbo-lower alkoxy-lower alkyl, phenyl-hydroxy-lower alkyl and lower alkenyl radicals and An is the anion of the strong acid. Illustrative of these esters are methyl sulfate, ethyl sulfate, methyl p-toluenesulfonate; lower alkyl halides, for example, methyl iodide, ethyl bromide, butyl bromide, and hexyl chloride; phenyl-lower alkyl halides, for example benzyl chloride, p-chlorobenzyl chloride, 2-chloro-4-methoxybenzyl chloride, and benzyl bromide; allyl and methallyl halides, for example, allyl bromide and methallyl chloride; carboxy-lower alkyl halides, for example chloroacetic acid, 3-chloro propionic acid, 2-bromo-propionic acid, cyano-lower alkyl halides, for exmaple, chloroacetonitrile and 3-bromopropionitrile; hydroxy-lower alkyl halides, for example 2,3-dihydroxypropyl chloride, ethylene chlorohydrin, ethylene bromohydrin, and isobutylene chlorohydrin; hydroxyoxaalkyl halides, for example, 2-hydroxy-3-(2,3-dihydroxypropoxy)propyl chloride and 2-hydroxy-2-[3-(2-hydroxyethoxy)ethoxy]propyl chloride; carbo-lower alkoxy-lower allyl halides, for example, methyl bromoacetate, ethyl 3-chloropropionate and butyl chloroacetate. Also useful as alkylating agents are lower alkylene oxides, for example, ethylene oxide, propylene oxide and epichlorohydrin; styrene oxide; p-chlorostyrene oxide; acrylonitrile; methacrylonitrile; and ethyl acrylate.

The N-monoalkylated compounds (Formula I where only one of $X_1$ and $X_2$ is NH) are obtained by heating preferably one or advantageously slightly more than one molecular equivalent of the appropriate alkylating agent with one molecular equivalent of the 4,4'-stilbenebis(2-imidazopyridine). Minor proportions of the corresponding N,N'-dialkylated compound (Formula I, where neither of $X_1$ and $X_2$ is NH) and of unreacted N,N'-unsubstituted starting material varying in amounts depending in part on the relative proportions of the reactants and in part on the reaction conditions, will be found associated with the N-monoalkylated compound obtained as the chief product of the alkylation reaction. If desired, the N-mono-alkylated product can be purified, for example by use of suitable solvents, but ordinarily it is unnecessary and uneconomical for practical purposes to effect such purification since the mixture is directly useful as a whitening and brightening agent.

As will be understood, the use of larger proportions of the alkylating agent favors higher yields of the N,N'-dialkylated compound. When this is the desired product, there are, of course, required by theory at least two molecular equivalents of the alkylating agent per equivalent of the 4,4'-stilbenebis(2-imidazopyridine); as a matter of fact, for best conversion to the dialkylated product an excess of the alkylating agent should be employed, for example an excess of 1-4 equivalents of the alkylating agent. The N,N'-dialkylated compounds obtained in this manner are symmetrical. When an unsymmetrical product is desired, an N-monoalkylated compound or, alternatively, a reaction mixture containing it is treated with a different alkylating agent, thereby producing a compound of Formula I wherein $X_1$ and $X_2$ contain different alkyl or substituted alkyl radicals.

When the alkylating agent has a hydroxyl group in its structure, for example, a hydroxy-lower alkyl or hydroxyoxaalkyl compound, the hydroxyl function in the resulting N-monoalkylated product (e.g., Formula I, $X_1$ = NH, $X_2$ = hydroxy-lower alkyl or hydroxy-oxaalkyl) interacts with a second equivalent of the same or a different alkylating agent to yield preferentially O-alkylated products rather than the expected N,N'-dialkylated derivative, the latter being produced only in relatively small amount. The use of a large excess of the alkylating agent leads to substantially complete production of N,N'-disubstituted products.

The compounds of my invention have been found to have high stability to heat and light and thus are well adapted for use as optical brightening agents by incorporation into melts of normally solid, fiber and film-forming polymeric material, for spinning synthetic fibers, or for casting or molding plastics in a concentration of from 0.005 to 0.5 percent by weight of the polymeric material. A further method utilizing the compounds of my invention is to impregnate textile fabrics comprising synthetic fibers, for example, polyester (poly[terephthalic acid ethyleneglycol ester]), poly-(1,4-cyclohexylenedimethylene terephthalate), or nylon, with an aqueous dispersion compound at temperatures below about 75°–100° C., for example, at room temperature, and then to subject the treated fabric to a dry heat treatment at a temperature above 100° C. The fabric may advantageously be dried at temperatures in the range 25°–100° C. prior to the heat treatment which is preferably carried out at temperatures in the range 125°–250° C. Said heat treatment may be accomplished by any of several known methods, for example, by heating in a dry chamber, by ironing the fabric, or by treating it with dry, super-heated steam.

The structures of the new compounds of my invention were determined by their mode of synthesis and by the correspondence of calculated and found values of elemental analyses of representative samples, and were corroborated by ultraviolet and infrared spectroanalyses.

The best mode contemplated for carrying out my invention will now be set forth in the following examples, which are given for the purpose of illustration without limiting the invention thereto:

EXAMPLE 1

4,4'-Stilbenebis(2-oxazolo[4,5-c]pyridine)

To 75 g. of polyphosphoric acid preheated to 100° C. was added 5.5 g. (0.02 mole) of 4,4'-stilbenedicarboxylic acid. The mixture was then further heated to 125° C. and 5.9 g. (0.04 mole) of 3-amino-4-pyridinol hydrochloride was added in small portions over a period of fifteen minutes. When the addition was complete, the mixture was heated with stirring at about 200° C. for 3½ hours. The resulting brown solution was poured into 375 ml. of water, and the mixture was stirred until the product congealed; the latter was collected on a filter, washed with water, and dried at 70° C. in vacuo.

The impure 4,4'-stilbenebis(2-oxazolo[4,5-c]pyridine) thus prepared was purified as follows: The product was stirred with aqueous sodium hydroxide at pH 10 and at 90°–95° C. for ½ hour. The remaining solid product was collected on a filter and was washed free of alkali with water. The dried product was then recrystallized from trichlorobenzene to give 4,4'-stilbenebis(2-oxazolo[4,5-c]pyridine) which melted at 345°–360° C. with decomposition. The gram extinction coefficient at the wavelength of maximum absorption of a solution of this compound in dimethylformamide was 122.8 at 370 nm. This compound has the structural formula

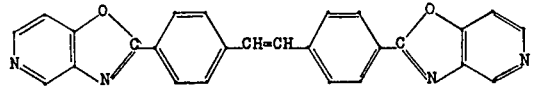

EXAMPLE 2A

Following a procedure similar to that described above in Example 1 but using 3-amino-2-pyridinol instead of 3-amino-4-pyridinol there is obtained 4,4'-stilbenebis-(2-oxazolo[5,4-b]pyridine), melting at 340°–360° C. with decomposition. The gram extinction coefficient for a solution of this product in dimethylformamide at the wavelength of maximum absorption was 178.0 at 376 nm. The structural formula of this compound is

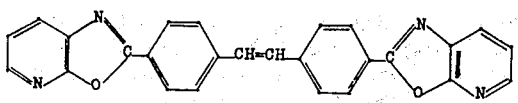

EXAMPLE 2B

In accordance with another procedure for preparing 4,4'-stilbenebis(2-oxazolo[5,4-b]pyridine) 8.5 ml. (0.163 mole) of thionyl chloride dissolved in 25 ml. of chloroform was added dropwise to 11.5 g. (0.03 mole) of dipotassium 4,4'-stilbenedicarboxylate suspended in 150 ml. of dry chlorobenzene. The mixture was refluxed for 3 hours, and the excess thionyl chloride was removed by distillation. To the resulting solution of 4,4'-stilbenedicarbonyl chloride in chlorobenzene was added 8.57 g. (0.06 mole) of 3-amino-2-chloropyridine in 50 ml. of dry chlorobenzene and 11.0 ml. of dry pyridine. The mixture was refluxed for 8.5 hours, and the solid product was collected on a filter and washed with chlorobenzene and with methanol. This intermediate, N,N'-bis(2-chloro-3-pyridyl)-4,4'-stilbenedicarboxamide, was purified by washing it chloride ion-free with water, drying, and recrystallizing from hot trichlorobenzene. The melting point of this product was 291°–293° C.

The above intermediate, N,N'-bis(2-chloro-3-pyridyl)-4,4'-stilbenedicarboxamide was cyclized to the desired 4,4'-stilbenebis(2-oxazolo[5,4,b]pyridine) as follows. To a solution containing 20 ml. of pyridine and 4.4 g. of cupric acetate monohydrate in 56 ml. of dimethylformamide was added 4.89 g. (0.01 mole) of N,N'-bis(2-chloro-3-pyridyl)-4,4'-stilbenedicarboxamide, prepared as above. The mixture was refluxed under nitrogen for about 6 hours, and then about 35 ml. of the solvent was removed by distillation. The residue was allowed to cool and the solid product was collected on a filter. It was triturated with concentrated hydrochloric acid to decompose and dissolve any copper complex, and it was then collected on a filter, washed free of acid with water, and dried under vacuum. The gram extinction coefficient of a dimethylformamide solution of 4,4'-stilbenebis(2-oxazolo[5,4-b]pyridine) thus prepared was 200.4 at 375 nm, its wavelength of maximum absorption.

When 4.16 g. (0.01 mole) of this product was refluxed in excess benzyl chloride in the presence of 2.12 g. of sodium carbonate there was obtained a quaternary ammonium salt having, in dimethylformamide solution, a gram extinction coefficient of 71.6 at 354 nm, the wavelength of maximum absorption.

EXAMPLE 3

To a suspension of 18.5 g. (0.05 mole) of dipotassium 4,4'-stilbenedicarboxylate in 250 ml. of dry chlorobenzene was added dropwise 13 ml. of thionyl chloride dissolved in 35 ml. of chlorobenzene. The mixture was refluxed for about three hours, and then 86 ml. of solvent was removed by distillation to remove all excess thionyl chloride. To the resulting solution of 4,4'-stilbenedicarbonyl chloride in chlorobenzene at about 80° C. was added 11.5 g. (0.1 mole) of 2-amino-3-pyridinol in 75 ml. of dry chlorobenzene and 9 ml. of pyridine. This mixture was refluxed for 10 hours and was allowed to cool to room temperature. The intermediate N,N'-bis(3-hydroxy-2-pyridyl)-4,4'-stilbenedicarboxamide hydrochloride was collected on a filter and was washed with chlorobenzene, methanol and water. The cake was then suspended in aqueous methanol and made alkaline with 10 percent aqueous sodium carbonate solution. The resulting N,N'-bis(3-hydroxy-2-pyridyl)-4,4'-stilbenedicarboxamide remained unmelted at 360° C. This intermediate product was ring-closed to 4,4'-stilbenebis(2-oxazolo[4,5-b]pyridine) by heating 9.0 g. of the dry product in 100 ml. of trichlorobenzene containing 9.6 g. of p-toluenesulfonic acid at 200°–210° C. for about 19 hours. The mixture was poured into water, neutralized, and collected on a filter. The product was purified by recrystallization from methanolic phenol. It was then poured into dilute aqueous sodium hydroxide, collected on a filter, and washed alkali-free with water. The 4,4'-stilbenebis(2-oxazolo[4,5-b]pyridine) thus obtained remained unmelted at 300° C. The gram extinction coefficient of this compound in dimethylformamide solution was 180.6 at 377 nm, the wavelength of maximum absorption. The compound has the structural formula

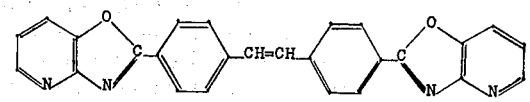

EXAMPLE 4

When 3-amino-4-pyridinethiol is substituted for 3-amino-4-pyridinol in Example 1 hereinabove there is obtained 4,4'-stilbenebis(2-thiazolo[4,5-c]pyridine). This compound has the structural formula

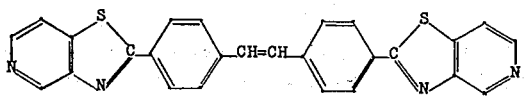

EXAMPLE 5

Following a procedure similar to that described above in Example 1, but using 4-amino-3-pyridinethiol instead of 3-amino-4-pyridinol there is obtained 4,4'-stilbenebis(2-thiazolo[5,4-c]pyridine). This compound has the structural formula

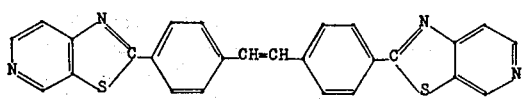

EXAMPLE 6

Following a procedure similar to that described above in Example 1 except that 2-amino-6-methyl pyridinethiol is used in place of 3-amino-4-pyridinol there is obtained 4,4′-stilbenebis(5-methyl-2-thiazolo[4,5-b]pyridine), having the structural formula

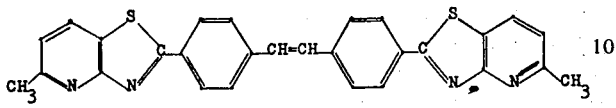

The intermediate 2-amino-6-methylpyridine is prepared as follows: To a solution of 68 g. (0.63 mole) of 2-amino-6-methylpyridine in about 500 ml. of glacial acetic acid, cooled to 10°–15° C., is added a mixture of 170.2 g. (2.1 moles) of sodium thiocyanate suspended in about 570 ml. of glacial acetic acid. A solution containing 30.5 ml. of bromine in about 60 ml. of glacial acetic acid is then added, and the mixture is stirred at 10°–15° C. for 1 hour and then at 75°–80° C. for ½ hour. The solution is filtered, and the solvent is removed from the filtrate under reduced pressure. The residue is recrystallized from isopropyl alcohol containing activated charcoal. The 2-amino-5-methyl-thiazolo[4,5-b]pyridine thus obtained melts at 150°–160° C. The product is hydrolyzed by refluxing 8 g. of the material in 120 ml. of 20 percent aqueous sodium hydroxide solution for 6 hours. The resulting cloudy solution is filtered, and the filtrate is acidified and reduced to dryness. The residue is extracted with hot ligroin to yield 2-amino-6-methyl-3-pyridinethiol, melting at 133°–138° C.

EXAMPLE 7

When 3-amino-2-pyridinethiol is substituted for 3-amino-4-pyridinol in Example 1 hereinabove there is obtained 4,4′-stilbenebis(2-thiazolo[5,4-b]pyridine), having the structural formula

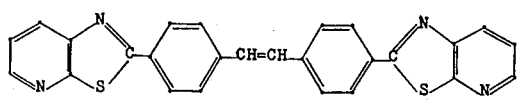

EXAMPLE 8

Following a procedure similar to that described above in Example 3 but using 3-amino-6-chloro-2-pyridinethiol instead of 2-amino-3-pyridinol there is obtained 4,4′-stilbenebis(5-chloro-2-thiazolo[5,4-b]pyridine), having the structural formula

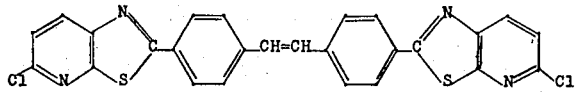

EXAMPLE 9

Following a procedure similar to that described above in Example 1 except that 3-amino-5-ethoxy-2-pyridinethiol is used in place of 3-amino-4-pyridinol there is obtained 4,4′-stilbenebis(6-ethoxy-2-thiazolo[5,4-b]pyridine), having the structural formula

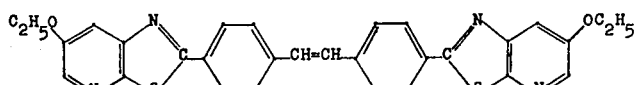

EXAMPLE 10

When 3-amino-6-methoxy-2-pyridinethiol is substituted for 2-amino-3-pyridinol in Example 3 hereinabove there is obtained 4,4′-stilbenebis(5-methoxy-2-thiazolo[5,4-b]pyridine), having the structural formula

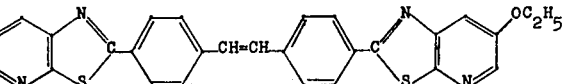

EXAMPLE 11

Following a procedure similar to that described above in Example 1 but using 3-amino-5-chloro-2-pyridinethiol instead of 3-amino-4-pyridinol there is obtained 4,4′-stilbenebis(6-chloro-2-thiazolo[5,4-b]pyridine), having the structural formula

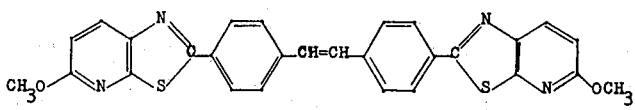

EXAMPLE 12

Following a procedure similar to that described above in Example 3 except that 3-amino-6-ethoxy-2-pyridinethiol is used in place of 2-amino-3-pyridinol there is obtained 4,4′-stilbenebis(5-ethoxy-2-thiazolo[5,4-b]pyridine), having the structural formula

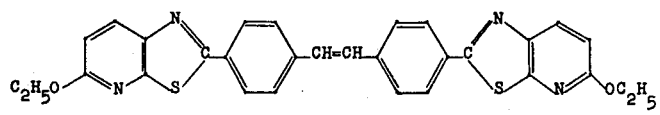

EXAMPLE 13

When 3-amino-5-bromo-4-pyridinethiol is substituted for 3-amino-4-pyridinol in Example 1 hereinabove there is obtained 4,4′-stilbenebis(7-bromo-2-thiazolo[4,5-c]pyridine), having the structural formula

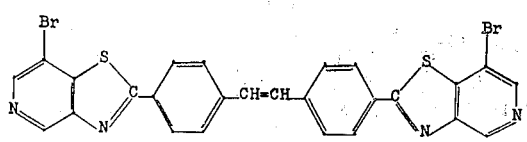

EXAMPLE 14

Following a procedure similar to that described above in Example 1, but using 4-amino-3-pyridinol instead of 3-amino-4-pyridinol there is obtained 4,4'-stilbenebis-(2-oxazolo[5,4-c]pyridine), having the structural formula

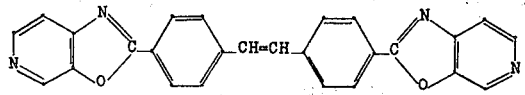

EXAMPLE 15

Following a procedure similar to that described above in Example 1 except that 3-amino-5-bromo-2-pyridinol is used in place of 3-amino-4-pyridinol there is obtained 4,4'-stilbenebis(6-bromo-2-oxazolo[5,4-b]pyridine), having the structural formula

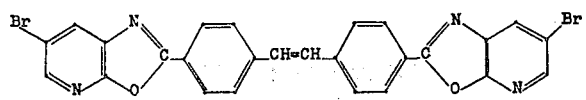

EXAMPLE 16

When 3-amino-5-chloro-2-pyridinol is substituted for 3-amino-4-pyridinol in Example 1 hereinabove there is obtained 4,4'-stilbenebis(6-chloro-2-oxazolo[5,4-b]pyridine), having the structural formula

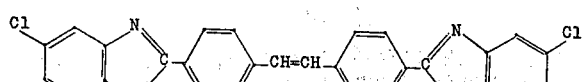

EXAMPLE 17

Following a procedure similar to that described above in Example 1 except that 3-amino-5-methyl-2-pyridinol is used in place of 3-amino-4-pyridinol there is obtained 4,4'-stilbenebis(6-methyl-2-oxazolo[5,4-b]pyridine), having the structural formula

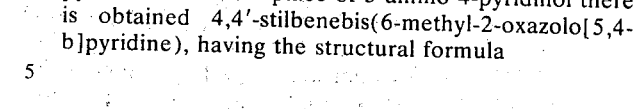

EXAMPLE 18

When 3-amino-6-propyl-2-pyridinol is substituted for 3-amino-4-pyridinol in Example 1 hereinabove there is obtained 4,4'-stilbenebis(5-propyl-2-oxazolo[5,4-b]pyridine), having the structural formula

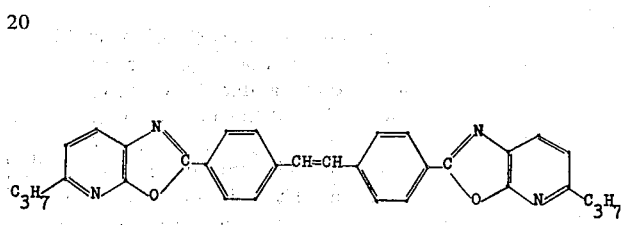

EXAMPLE 19

Following a procedure similar to that described above in Example 1 but using 3-amino-6-methyl-2-pyridinol instead of 3-amino-4-pyridinol there is obtained 4,4'-stilbenebis(5-methyl-2-oxazolo[5,4-b]pyridine), having the structural formula

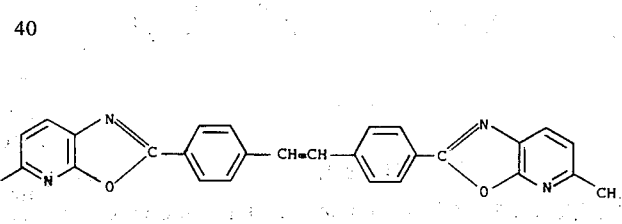

EXAMPLE 20

Following a procedure similar to that described above in Example 1 except that 3-amino-5-bromo-4-pyridinol is used in place of 3-amino-4-pyridinol there is obtained 4,4'-stilbenebis(7-bromo-2-oxazolo[4,5-c]pyridine), having the structural formula

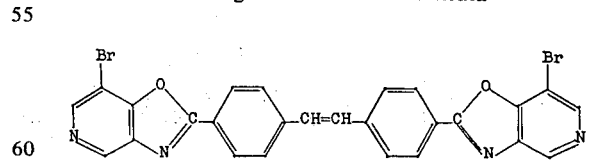

EXAMPLE 21

To 17.3 g. (0.05 mole) of dipotassium 4,4'-stilbenedicarboxylate in 250 ml. of chlorobenzene was added dropwise and with stirring 21.3 g. (0.18 mole) of thionyl chloride in 35 ml. of chlorobenzene. The mixture was refluxed for 3 hours and about half of the solvent was removed by distillation to remove all traces of excess thionyl chloride. The resulting solution of 4,4'-stilbenedicarbonyl chloride in chlorobenzene was cooled to 65° C., and 11.4 g. (0.105 mole) of 2,3-diaminopyridine was added portionwise, followed by 9 ml. (0.1 mole) of pyridine in 75 ml. of dry chlorobenzene. The mixture was heated to reflux whereupon an exothermic reaction started; reflux was continued for 10 hours. After cooling the mixture, the product was collected on a filter and washed thoroughly with chlorobenzene and methanol. The product was then triturated with sodium carbonate solution, washed free of chloride ion with distilled water, and dried. The resulting N,N'-bis(3-amino-2-pyridyl)-4,4'-stilbenedicarboxamide remained unmelted at 310° C. Infrared spectral analysis of the product showed a strong band at 1645 $cm^{-1}$, indicative of the presence of an amide carbonyl. The ultraviolet absorption spectrum showed maxima at 361 and 377 nm.

The above-described bis(aminocarboxamide) was cyclized as follows: To 9.0 g. of the above product in 100 ml. of dry trichlorobenzene was added 7.6 g. (0.04 mole) of p-toluenesulfonic acid, and the mixture was refluxed under an atmosphere of nitrogen for about 27 hours, whereupon the maximum absorption peak at 361 nm. essentially disappeared. The mixture was allowed to cool, and the product which separated was collected on a filter and was washed with trichlorobenzene and then methanol. The 4,4'-stilbenebis(2-imidazo[4,5-b]pyridine) thus obtained, purified by reprecipitation from aqueous alkaline methanol, remained unmelted at 300° C. and had the structural formula

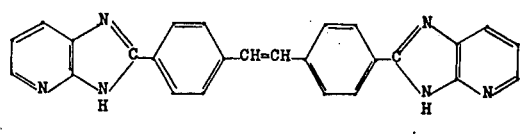

EXAMPLE 22

Following a procedure similar to that described above in Example 21, but using 3-diamino-6-chloropyridine instead of 2,3-diaminopyridine there is obtained 4,4'-stilbenebis(5-chloro-2-imidazo[4,5-b]pyridine), having the structural formula

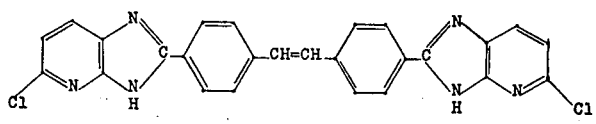

EXAMPLE 23

Following a procedure similar to that described above in Example 21 except that 2,3-diamino-5-bromopyridine is used in place of 2,3-diaminopyridine there is obtained 4,4'-stilbenebis(6-bromo-2-imidazo[4,5-b]pyridine, having the structural formula

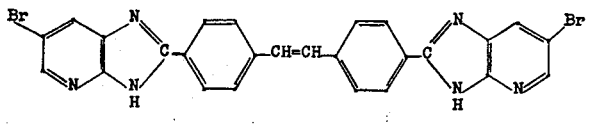

EXAMPLE 24

When 2,3-diamino-5-chloropyridine is substituted for 2,3-diaminopyridine in Example 21 hereinabove there is obtained 4,4'-stilbenebis(6-chloro-2-imidazo[4,5-b]pyridine), having the structural formula

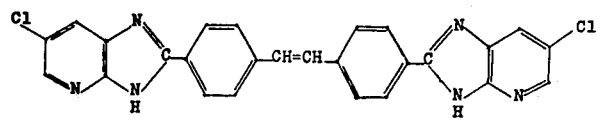

EXAMPLE 25

Following a procedure similar to that described above in Example 21 but using 2,3-diamino-5,6-dichloropyridine instead of 2,3-diaminopyridine there is obtained 4,4'-stilbenebis(5,6-dichloro-2-imidazo[4,5-b]pyridine), having the structural formula

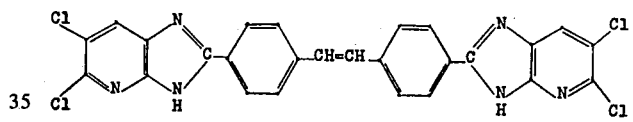

EXAMPLE 26

Following a procedure similar to that described above in Example 21 except that 2,3-diamino-4,5,6-trimethylpyridine is used in place of 2,3-diaminopyridine there is obtained 4,4'-stilbenebis(5,6,7-trimethyl-2-imidazo[4,5-b]pyridine), having the structural formula

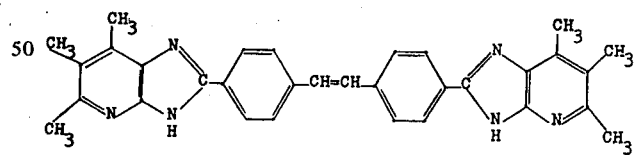

EXAMPLE 27

When 2,3-diamino-6-propylpyridine is substituted for 2,3-diaminopyridine in Example 21 hereinabove there is obtained 4,4'-stilbenebis[5-propyl-2-imidazo[4,5-b]pyridine), having the structural formula

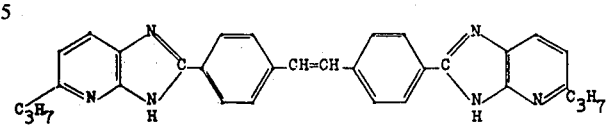

EXAMPLE 28

Following a procedure similar to that described above in Example 21 but using 3,4-diaminopyridine instead of 2,3-diaminopyridine there is obtained 4,4'-stilbenebis-(2-imidazo[4,5-c]pyridine), having the structural formula

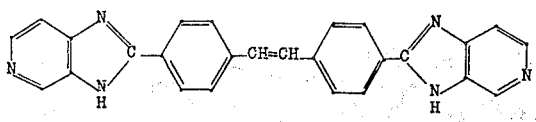

EXAMPLE 29

Following a procedure similar to that described above in Example 21 except that 3,4-diamino-2-chloropyridine is used in place of 2,3-diaminopyridine there is obtained 4,4'-stilbenebis(4-chloro-2-imidazo[4,5-c]pyridine), having the structural formula

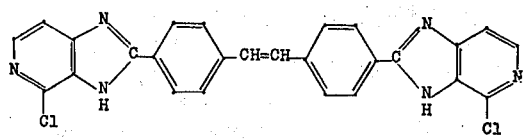

EXAMPLE 30

When 3,4-diamino-5-bromopyridine is substituted for 2,3-diaminopyridine in Example 21 hereinabove there is obtained 4,4'-stilbenebis(7-bromo-2-imidazo[4,5-c]pyridine), having the structural formula

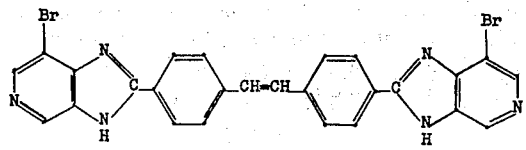

EXAMPLE 31

Following a procedure similar to that described above in Example 21 but using 3,4-diamino-2,5,6-trifluoropyridine instead of 2,3-diaminopyridine there is obtained 4,4'-stilbenebis(4,6,7-trifluoro-2-imidazo[4,5-c]pyridine), having the structural formula

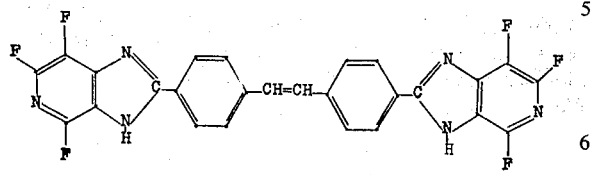

EXAMPLE 32

Following a procedure similar to that described above in Example 21 except that 3,4-diamino-2,6-dichloropyridine is used in place of 2,3-diaminopyridine there is obtained 4,4'-stilbenebis(4,6-dichloro-2-imidazo[4,5-c]pyridine), having the structural formula

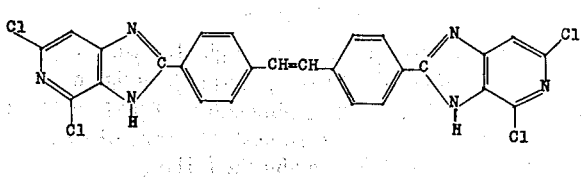

EXAMPLE 33

When 3-amino-5-methyl-2-pyridinethiol is substituted for 3-amino-4-pyridinol in Example 1 hereinabove there is obtained 4,4'-stilbenebis(6-methyl-2-thiazolo[5,4-b]-pyridine), having the structural formula

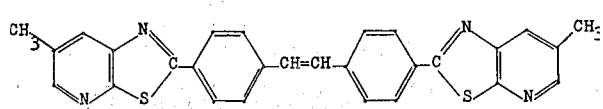

EXAMPLE 34

Following a procedure similar to that described above in Example 2B but using 2-methyl-4,4'-stilbenedicarboxylic acid instead of 4,4'-stilbenedicarboxylic acid there is obtained 2-methyl-4,4'-stilbenebis(2-oxazolo[5,4-b]pyridine), having the structural formula

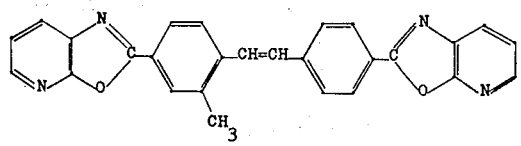

EXAMPLE 35

Following a procedure similar to that described above in Example 2B except that 2,2'-dimethyl-4,4'-stilbenedicarboxylic acid is used in place of 4,4'-stilbenedicarboxylic acid there is obtained 2,2'-dimethyl-4,4'-stilbenebis-(2-oxazolo[5,4-b]pyridine), having the structural formula

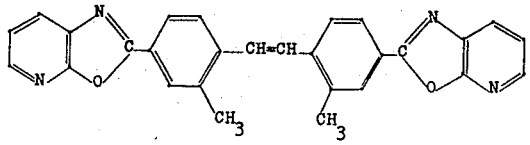

EXAMPLE 36

To 4.1 g. (0.01 moles) of 4,4'-stilbenebis(2-imidazo[4,5-b]pyridine) (Example 21) dissolved in 25 ml. of 2-methoxyethanol containing 1.6 g. of 50 percent aqueous sodium hydroxide solution is added 1.1 g. (0.02 mole) of acrylonitrile. The mixture is heated at approximately 50° for 2 hours, whereupon there is obtained 4,4'-stilbenebis-[1-(2-cyanoethyl)-2-imidazo[4,5-b]pyridine], having the formula

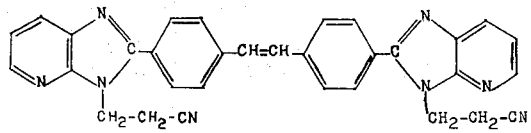

EXAMPLE 37

Following the procedure of Example 36, using 4,4'-stilbenebis(2-imidazo[4,5-c]pyridine) (Example 28) in place of 4,4'-stilbenebis(2-imidazo[4,5-b]pyridine), there is obtained 4,4'-stilbenebis[1-2-cyanoethyl)-2-imidazo[4,5-c]-pyridine], having the formula

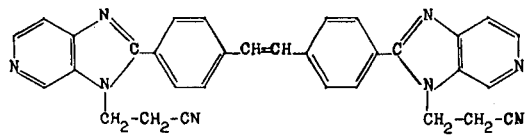

EXAMPLE 38

When 4,4'-stilbenebis[1-(2-cyanoethyl)-2-imidazo[4,5-b]pyridine) (Example 36) is refluxed in excess dilute sodium hydroxide for two hours, acidified and filtered, there is obtained the hydrolysis product, 4,4'-stilbenebis[1-(2-carboxyethyl)-2-imidazo[4,5-b]pyridine] of the formula

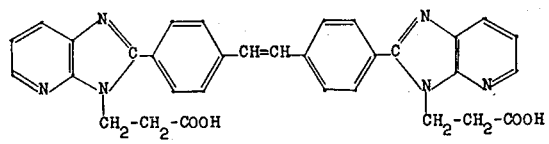

EXAMPLE 39

Following the procedure given in Example 38, using 4,4'-stilbenebis[3-(2-cyanoethyl)-2-imidazo[4,5-c]pyridine] (Example 37) in place of 4,4'-stilbenebis[3-(2-cyanoethyl)-2-imidazo[4,5-b]pyridine] there is obtained 4,4'-stilbenebis[1-(2-carboxyethyl)-2-imidazo[4,5-c]pyridine] of the formula

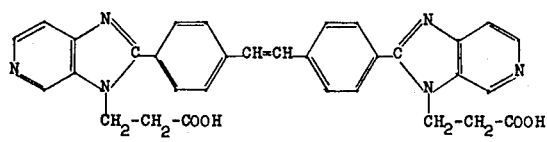

EXAMPLE 40

Following the procedure of Example 36, using one molecular proportion of acrylonitrile for each molecular proportion of 4,4'-stilbenebis(2-imidazo[4,5-b]pyridine) there is obtained 4-[3-(2-cyanoethyl)-2-imidazo[4,5-b]-pyridino]-4'-(2-imidazo[4,5-b]pyridino)stilbene of the formula

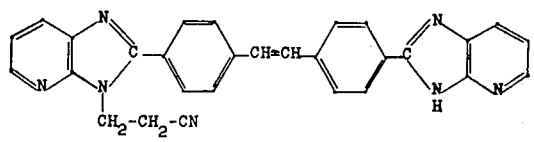

EXAMPLE 41

Following the procedure of Example 36, using two molecular equivalents of dimethylsulfate instead of acrylonitrile, there is obtained 4,4'-stilbenebis(3-methyl-2-imidazo[4,5-b]pyridine) of the formula

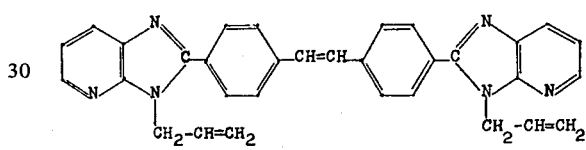

EXAMPLE 42

Following a procedure similar to that described above in Example 36, but using two molecular equivalents of allyl chloride instead of acrylonitrile there is obtained 4,4'-stilbenebis(3-allyl-2-imidazo[4,5-b]pyridine) of the formula

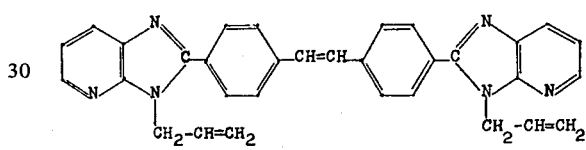

EXAMPLE 43

Following a procedure similar to that described above in Example 41 except that one molecular equivalent of dimethyl sulfate is used in place of two molecular equivalents, there is obtained 4-(2-imidazo[4,5-b]pyridino)-4'-(3-methyl-2-imidazo[4,5-b]pyridino)-stilbene having the formula

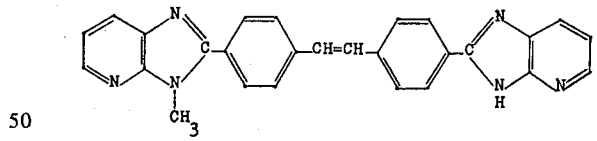

EXAMPLE 44

When benzyl chloride is substituted for acrylonitrile in Example 36 hereinabove there is obtained 4,4'-stilbenebis(3-benzyl-2-imidazo[4,5-b]pyridine) of the formula

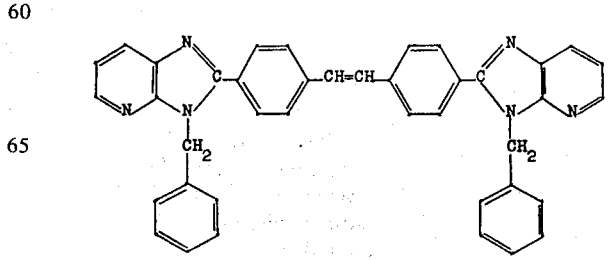

EXAMPLE 45

Following a procedure similar to that described above in Example 36, but using three molecular equivalents of 2,3-dihydroxypropyl chloride instead of acrylonitrile there is obtained 4-[3-(2,3-dihydroxypropyl)-2-imidazo[4,5-b]-pyridino]-4'-[3-(3-[2,3-dihydroxypropoxy]-2-hydroxypropyl)-2-imidazo[4,5-b]pyridine]stilbene of the formula

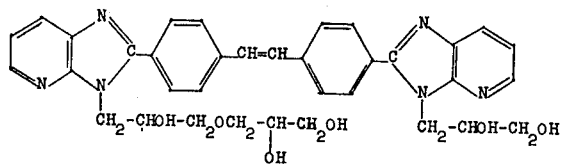

EXAMPLE 46

When the reaction mixture containing the above compound (Example 45) is refluxed with another one molecular equivalent of 2,3-dihydroxypropyl chloride, there is obtained a product consisting chiefly of 4,4'-stilbenebis(3-[2-hydroxy-3-(2,3-dihydroxypropoxy)-propyl]-2-imidazo[4,5-b]pyridine) of the formula

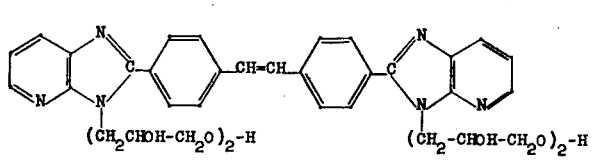

EXAMPLE 47

Following a procedure similar to that described above in Example 36, but using two molecular equivalents of ethyl acrylate instead of acrylonitrile there is obtained 4,4'-stilbenebis(3-[2-carbethoxyethyl]-2-imidazo[4,5-b]pyridine) of the formula

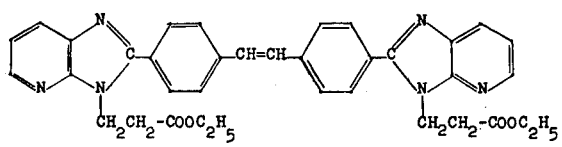

EXAMPLE 48

Following a procedure similar to that described above in Example 36 except that 2 molecular equivalents of ethylene oxide are used in place of acrylonitrile there is obtained 4,4'-stilbenebis(3-[2-hydroxyethyl]-2-imidazo[4,5-b]-pyridine) of the formula

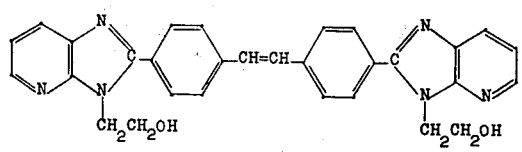

EXAMPLE 49

When two molecular equivalents of styrene oxide are substituted for ethylene oxide in Example 48 hereinabove there is obtained 4,4'-stilbenebis(3-[2-hydroxy-2-phenylethyl]-2-imidazo[4,5-b]pyridine) of the formula

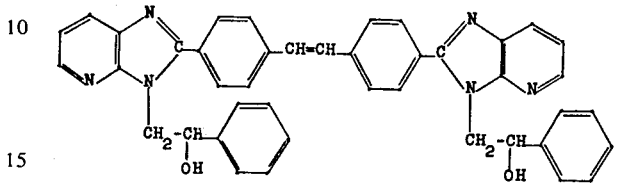

EXAMPLE 50

Following a procedure similar to that described above in Example 36, but using two molecular equivalents of o-chlorobenzyl chloride instead of acrylonitrile there is obtained 4,4'-stilbenebis(3-[o-chlorobenzyl]-2-imidazo[4,5-b]-pyridine) of the formula

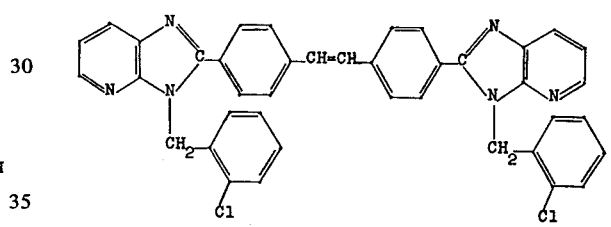

EXAMPLE 51

Following a procedure similar to that described above in Example 36 except that one molecular equivalent of p-chlorostyrene oxide is used in place of acrylonitrile there is obtained 4-(2-imidazo[4,5-b]pyridino)-4'-(3-[2-(2-hydroxy-2-p-chlorophenyl)ethyl]-2-imidazo[4,5-b]pyridine) of the formula

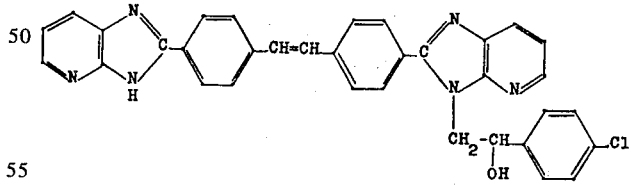

The effectiveness of the optical brightening agents, prepared as above, when incorporated into polyethylene terephthalate melts, was tested as follows:

A solution of 4,4'-stilbenebis(2-oxazolo[5,4-b]-pyridine) (Example 14A) in dimethyl terephthalate was prepared by intermixing 0.04 gr. of the brightener with 10.00 gr. of dimethyl terephthalate and then melting the two solids together, with continual stirring and under a carbon dioxide atmosphere, by immersing the container in a bath of diethyl phthalate maintained at 200° C. After about 15-20 minutes the fluid mixture was poured into a mortar and ground to a fine powder. The solid solution of brightener in dimethyl phthalate was incorporated into polyethylene terephthalate by blending 1.0 g. of the brightener-dimethyl terephthalate powder with 19.0 g. of predried polyethylene terephthalate chips. The mixture was melted under a carbon dioxide atmosphere by immersing the container in a bath of diethyl phthalate which was heated to boiling (295°-7° C.). The melt was stirred for 5 minutes, and it then was removed from the bath and allowed to cool to room temperature, continually under carbon dioxide. The polyethylene terephthalate casting was then broken up and ball milled with stoneware pellets in distilled water. The particles were dried and screened, and those passing through a 40 mesh screen were packed into a 5 cm. Petri dish. The color of the sample was then measured on a color difference meter (Hunterlab Model D-25, Hunter Associates Laboratory, McLean, Va.) in comparison with a standard magnesium oxide plate. These values were then compared with a blank sample prepared in the identical way except that the optical brightener was omitted. Following are the readings obtained in comparison with the standard magnesium oxide plate:

Hunterlab D-25 Readings

| | L | a | b |
|---|---|---|---|
| Blank polyethylene terephthalate (PET) | 98.6 | +0.4 | +0.9 |
| PET containing 0.02 per cent 4,4'-stilbenebis(2-oxazolo[5,4-b]pyridine) | 99.0 | +2.9 | −6.0 |

These results show that the shade of whiteness imparted to the polyethylene terephthalate was in the pink and blue range considered most desirable in the textile art. For the significance of the values recorded above, see R. S. Hunter, Photoelectric Color Difference Meter, J. Opt. Soc. Am., 48, 985 (1958).

1. A fluorescent compound of the formula

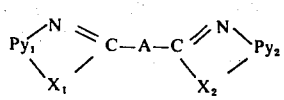

wherein $Py_1$ and $Py_2$ are each a bivalent heterocyclic nucleus of the pyridine class in which the open bonds are on vicinal ring carbon atoms of said nucleus wherein each of the pyrido rings is otherwise unsubstituted or further substituted by a member of the class consisting of halogen, lower alkoxy and lower alkyl; $X_1$ and $X_2$ are each a member of the class consisting of O, S and NR, wherein R is H, lower alkyl, hydroxy-lower alkyl, hydroxyoxaalkyl of 3 to 15 carbon atoms, phenyl-lower alkyl, cyano-lower alkyl, carboxy-lower alkyl, carbo-lower alkoxy-lower alkyl, phenyl-hydroxy-lower alkyl or lower alkenyl; and A is a bivalent 4,4'-stilbene radical of the formula

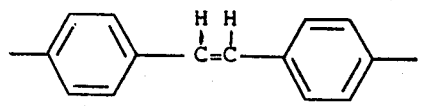

2. A fluorescent compound according to claim 1 of the formula

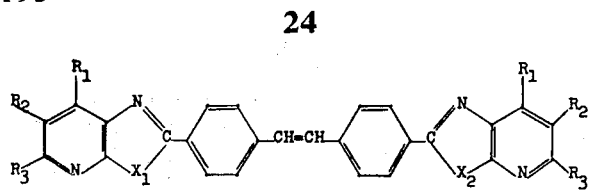

wherein each of $R_1$, $R_2$ and $R_3$ is H, halogen, lower alkoxy or lower alkyl and $X_1$ and $X_2$ are as defined in Claim 1.

3. A fluorescent compound according to claim 1 of the formula

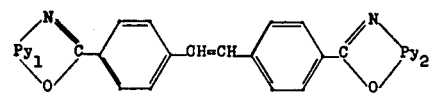

wherein $Py_1$ and $Py_2$ are as defined in claim 1.

4. The fluorescent compound according to claim 3 of the formula

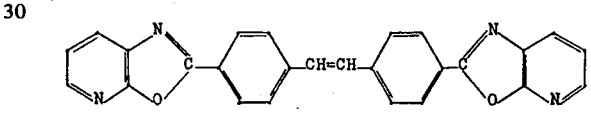

5. The fluorescent compound according to claim 3 of the formula

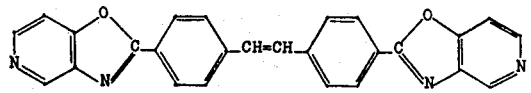

6. The fluorescent compound according to claim 3 of the formula

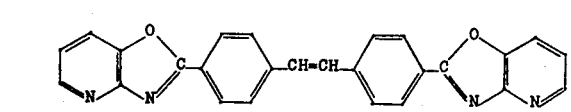

7. The fluorescent compound according to claim 2 of the formula

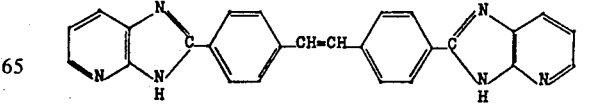

* * * * *

UNITED STATES PATENT AND TRADEMARK OFFICE
CERTIFICATE OF CORRECTION

PATENT NO. : 3,935,195
DATED : January 27, 1976
INVENTOR(S) : Nathan N. Crounse

It is certified that error appears in the above-identified patent and that said Letters Patent are hereby corrected as shown below:

Column 1, line 36, "hydromyon-" should read -- hydroxyox- --.

Column 4, line 26, "teh" should read -- the --.

Column 4, line 48, "easy" should read -- ease --.

Column 6, line 20, "[5,4b]" should read -- [5,4-b] --.

Column 6, line 42, "[4.5-b]" should read [4,5-b] --.

Column 6, line 65, "exmaple" should read -- example --.

Column 8, line 3, "poly-(" should read -- poly( --.

Column 23, line 42, insert -- I claim: -- before Claim 1.

Signed and Sealed this

Thirteenth Day of June 1978

[SEAL]

Attest:

RUTH C. MASON
Attesting Officer

DONALD W. BANNER
Commissioner of Patents and Trademarks